(12) United States Patent
Vito (10) Patent No.: US 7,832,393 B2
(45) Date of Patent: Nov. 16, 2010

(54) SPACER/HOLDING CHAMBER FOR PRESSURIZED METERED DOSE INHALER

(76) Inventor: John Vito, 2 Meadowside Cir. R.R. 1, Box 354-1, Dalton, PA (US) 18414

( * ) Notice: Subject to any disclaimer, the term of this patent is extended or adjusted under 35 U.S.C. 154(b) by 804 days.

(21) Appl. No.: 11/825,086

(22) Filed: Jul. 3, 2007

(65) Prior Publication Data

US 2009/0007905 A1  Jan. 8, 2009

(51) Int. Cl.
  *A61M 11/00* (2006.01)
(52) U.S. Cl. .............................. 128/200.23; 128/200.12
(58) Field of Classification Search ............ 128/200.11, 128/200.12, 200.14, 200.22, 200.23, 203.12, 128/203.15, 203.18, 203.21, 203.19, 205.24, 128/202.27, 202.21; 604/57.58
See application file for complete search history.

(56) References Cited

U.S. PATENT DOCUMENTS

| | | | |
|---|---|---|---|
| 2,865,370 A | 12/1958 | Gattone | |
| 3,001,524 A | 9/1961 | Maison et al. | |
| 3,998,226 A | 12/1976 | Harris | |
| 4,637,528 A * | 1/1987 | Wachinski et al. | 222/182 |
| 4,953,545 A | 9/1990 | McCarty | |
| 5,012,803 A | 5/1991 | Foley et al. | |
| 5,074,294 A | 12/1991 | Chiesi | |
| 5,368,016 A | 11/1994 | Henry | |
| 5,507,278 A | 4/1996 | Karell | |
| 5,746,197 A | 5/1998 | Williams | |
| 5,809,996 A | 9/1998 | Alldredge | |
| 6,257,231 B1 * | 7/2001 | Shick et al. | 128/200.14 |
| 6,435,177 B1 * | 8/2002 | Schmidt et al. | 128/200.23 |
| 6,595,206 B2 | 7/2003 | Vito | |

FOREIGN PATENT DOCUMENTS

| | | |
|---|---|---|
| EP | 0015247 | 1/1980 |
| EP | 0074937 | 7/1982 |
| GB | 2110543 | 12/1981 |
| GB | 2182249 | 5/1987 |

* cited by examiner

*Primary Examiner*—Steven O Douglas
(74) *Attorney, Agent, or Firm*—Kenneth P. Glynn, Esq.

(57) ABSTRACT

A metered dosage inhaler device having a first member for receiving and dispensing inhalation medication which is hollow, and has an aerosol medication container insertion end and having a nozzle end for spraying medication into a mouth of a user, wherein the nozzle end has a defined length and has an orifice with a defined cross-sectional area outlet surfaces, inner surfaces and a defined outer perimeter at its termination. There is a second member, the second member which is a spacer fitted on the nozzle and adapted to move outwardly and inwardly relatively to the nozzle, the spacer being hollow and being located about either outer surfaces or within the inner surfaces of the nozzle, the spacer having a total length about equal to or less than the nozzle so as to preserve significant compactness when the spacer is moved inwardly relative to the nozzle. The spacer includes a plurality of movable segments such as telescopic ring segments. The first member has a tube with a reciprocal sleeve for holding a medication container and cooperates to permit full insertion of the segments into the first member.

20 Claims, 6 Drawing Sheets

SPACER/HOLDING CHAMBER FOR PRESSURIZED METERED DOSE INHALER

BACKGROUND OF INVENTION a. Field of Invention

The present invention inhaler is a metered dose inhaler for medication delivered from aerosol container. It includes an extendable spacer device which extends outwardly and closes inwardly relative to the nozzle inhaler in such a way that the extendable spacer device preserves significant compactness by having a total length about equal to or less than the nozzle length in its contracted form. Compactness is further achieved by a b. Description of Related Art The following patents describe metered dose inhalers with various adaptations, i.e. extendable spacers and related devices:

U.S. Pat. No. 6,595,206 B2 describes a metered dosage inhaler device having a main housing member for receiving and dispensing inhalation medication that is hollow, and has an aerosol medication container insertion end and a nozzle portion, wherein the nozzle has a defined length and has an orifice with a defined cross-sectional area outlet surfaces and inner surfaces. There is a spacer member, fitted on the nozzle and adapted to move outwardly and inwardly relatively to the nozzle, the spacer being hollow and being located about either outer surfaces or within the inner surfaces of the nozzle, the spacer having a total length about equal to or less than the nozzle on the outside, or at least half of its length within the device when on the inside, so as to preserve significant compactness. The spacer member includes a plurality of moveable segments such as telescopic rings, bellows segment or popoid segments.

U.S. Pat. No. 5,809,996 describes a disclosed inhalation apparatus is suited for easily administering aerosol medication via a metered does pressurized canister. The apparatus has a collapsible tubular body comprised of axially nested ridged pieces including end pieces with opposite connections respectively for directing spray from the canister axially through the tubular body cavity from one connection toward the other connection serving as the user's tubular mouthpiece. The tubular body can be axially shifted between an expanded operational position of maximum body cavity volume and maximum separation between the end pieces and a collapse storage position of minimum separation where the rigid pieces are nested together. The end pieces have end plates of substantially equal size with peripheries suited to be gripped by the user, and a tubular flange projected off of one plate that cooperates in proximity with structure of the other end plate that in the collapse position, providing a protective housing overlying the rigid pieces when collapsed.

U.S. Pat. No. 5,746,197 describes an extension that is attachable to metered dose inhalers for more effective and efficient delivery of the medication to the lungs of the user. The extension comprises a member having a bore therethrough that is sized and configured at a first end to match the size and shape of the inhaler nozzle, tapers to a reduced cross-section and extends with a generally uniform cross-section for at least one inch to the second end so as to force the user to slowly inhale the medication into the lungs. An adaptor attached to the first end of the member receives the nozzle therein so that the nozzle is in fluid flow communication with the bore of the member. A portion of the member, including the second end, defines a mouthpiece at least one and one half inches long that is receivable in the mouth of a user.

U.S. Pat. No. 5,507,278 describes an inhaler for asthma and other medical conditions which consists of a medicine canister and a canister holder. A tongue guard for the inhaler is attached onto the canister holder, and assists the user in placing the inhaler into the proper position. When the inhaler is activated, flow of medicine is diverted away from the tongue, thereby preventing bad taste and injury to tongue, such as atrophy. It can be used in conjunction with spacer devices or it can be built integrally within canister holder.

U.S. Pat. No. 5,368,016 provides for improved delivery of anaesthetic to an airway. By the invention, topical airway anesthesia is passively provided. A method in accordance with the invention, provides for release of a suitable anaesthetic in aerosolized form from a canister containing the anaesthetic, and utilizes an oropharyngeal airway.

U.S. Pat. No. 5,074,294 describes an apparatus for the administration of drugs in form of metered aerosol, consisting of an expansion chamber comprising two coaxial tubes freely slidable within one another and detachable. The external tube has an open end and a tapered end on which the chamber mouthpiece is mounted. The internal tube has an open end which may be inserted into the external tube and on opposite end on which the mouthpiece of a conventional dispenser containing the active principle in form of pressurized aerosol is stuck. The apparatus allows a better penetration of the drug into the airways up to the deepest zones of the bronchial tree.

U.S. Pat. No. 5,012,803 describes a medical inhaler which has a cylindrical body usable with different inlet and outlet fittings at the opposite ends thereof. An inlet end fitting is provided with inner and outer cylindrical flanges gripping the upstream end of the cylindrical body and adapted to receive structure for misting medication into said cylindrical body. The downstream or outlet end fittings snaps over the downstream end of the cylindrical body and is provided with an axially extending protrusion impinging against and securing a flexible diaphragm to an inwardly directed flange at the exit end of the cylindrical body. The outlet end fitting may take different forms such as a mouthpiece to fit into a patient's mouth, a mask to fit over a patient's mouth and nose, or a connection for flexible tubing leading to an endotracheal tube.

U.S. Pat. No. 4,953,545 describes a disposable, independent hand-held chamber for the purpose of dispersing aerosol respiratory medication delivered from metered-dose inhalers that comprises an elongated tapered chamber with an aperture on smaller end for insertion of metered-dose inhaler and mouth piece on larger end for inhalation of released aerosol medication.

U.S. Pat. No. 3,998,226 describes an inhalation devise for encapsulated concentrates having a capsule piercing hypodermic needle, a mouthpiece and a cavity for receiving a capsule containing a granular medicant and the like, whereby the device is actuated to pierce the capsule to form a pair of aligned openings. An aerosol bottle is so mounted on the device that fluid under pressure is conducted through the hypodermic needle and through the aligned openings in the capsule to disperse particles of the medicant thereby. The mixture of fluid under pressure and particles of medicant are then discharged through a venturi passageway in the mouthpiece and into a person's mouth.

U.S. Pat. No. 3,001,524 is directed to a device suitable for use in combination with an aerosol dispensing container equipped with a metering valve means and charged with a medicament-containing, self-propelling liquid composition, which comprises in combination an aerosol dispensing container charged with a medicament-containing, self-propelling liquid composition and equipped with metering valve, and a means for actuating said metering valve means and a delivery tube member so shaped and so proportioned as to conform to an oral cavity of the user and capable of administering into a body cavity a measured dose of medicament in aerosol form substantially free of droplets of unvaporized, liquid propellant to accomplish inhalation therapy, said actuating means being equipped with air inlet means between it and said dispensing container permitting scavenging of the medicament-containing aerosol from the tube into the body cavity of the user, said delivery tube member being of substantially straight longitudinal axis and of sufficient length to deliver a dose of medicament substantially free of unvaporized liquid propellant while preventing substantial loss of medicament-containing aerosol, said device being small enough to transport in the pocket of the user, said container and said actuating means being usable in detachable engagement with each other.

U.S. Pat. No. 2,865,370 describes a dispensing adaptor for use with disposable aerosol units having a hollow valve stem, comprising a hollow body formed with a coupling skirt, a centrally apertured plate mounted in the body above the skirt engagable over the valve stem, valve operating means carried by the body positioned above the end of the valve stem, and a discharge nozzle extending from the said body, said valve operating means including a curved surface, said surface being directed toward the discharge end of said discharge nozzle by index means formed in said aerosol units and said skirt portion of the body.

U.K. Patent No. 2,182,249 describes a compressible nebuhaler which has a spindle shaped, transparent polythane bag like the bellows of an accordion which is attached at either end to the centers of circular discs and encircling the openings of the mouthpiece and the opening for the insertion of an aerosol. Aerial like or "telescopic" metallic rods around the spindle shaped compressible chamber expand or compress the nebuhaler chamber by lengthening or shortening when appropriate pressure is applied. The compressed nebuhaler has a shape of a "burger" and can easily be carried in a vanity bag or school bag.

U.K. Patent No. 2,110,543 describes an inhalation chamber for use with a supply of aerosol-propelled medication, comprises a mouthpiece 15 and a set of clear plastics, telescoping rings 7A to 7J, and 6, which define, in their extended position, the inhalation chamber. The inhalation chamber through the smallest ring 7A e.g. from an aerosol. The user may then draw on the mouthpiece 15 to open a non-return valve in an end wall 5 of the chamber, and inhale the medication. The chamber may be collapsed, the rings then adopting their nested position within a casing formed by the end wall 5 and the outermost ring 6. A detachable cover is engaged over the open end of the latter. The inhaler components may thus, fit readily into the user's pocket or handbag.

U.K. Patent No. 0,074,937 describes an aerosol inhalation device in pocket size which has on dosage dispensing position and one storage position, and which comprises a two part telescoping deceleration chamber with rectangular cross section and a socket for an exchangeable aerosol container. The socket is connected with the inner chamber part so that it can be telescopically inserted therein to form a storage position. In dosage dispensing position the socket is extended from the deceleration chamber, pivoted at an angle relative the longitudinal axis of the chamber and locked in said angle.

U.K. S. Patent No. 0,015,247 describes an aerosol inhalation device comprising an elongated chamber, an outer chamber part of which has an outlet opening and is telescopically displaceable over an inner chamber part which is connectable to an aerosol dispenser and provided with a flexible tongue which on telescoping the device together closes the outlet opening.

Notwithstanding the prior art, the present invention is neither taught nor rendered obvious thereby.

SUMMARY OF INVENTION

The present invention relates to a pressurized metered dosage inhaler device having a main housing member for receiving and dispensing inhalation medication, the main housing member being hollow, and having an aerosol medication container insertion tube and a central axis of direction of insertion of an aerosol medication container, and having a nozzle portion for spraying medication into a mouth of a user, the nozzle portion extending away from the central axis, wherein the nozzle portion includes a nozzle segment that that is exterior from the main housing member and has a defined length L, and has an orifice with a defined cross-sectional area outer surfaces, inner surfaces. More specifically the improvement comprises: a spacer member, the spacer member being fitted onto the nozzle segment and adapted to move outwardly and inwardly relatively to the nozzle segment, the spacer member being hollow and being located about the outer surfaces of the nozzle segment, the spacer member including a plurality of moveable segments, each of the moveable segments being interconnected with one another, the spacer member having an open extended position with the moveable segments being extended relative to one another to create an elongated spacer member, wherein an outermost extended segment is a mouthpiece segment, and the spacer member having a closed position wherein all of the moveable segments are collapsed relative to one another such that all moveable segments are located about the nozzle, so as to have a total length equal to or less than exterior nozzle segment length L so as to eliminate protrusion beyond the nozzle segment, and so as to preserve significant compactness when the spacer member is moved inwardly relative to the nozzle; and, an aerosol medication container sleeve connected to and partially located inside the aerosol medication container tube, the sleeve being reciprocally slideable along the central axis and relative to the tube, the sleeve being adapted to receive and hold an aerosol medication container, the sleeve having a first, open position wherein the sleeve is extended away from the main housing member to create a maximum open internal volume for collapse of the spacer segments into the main housing, the sleeve having a second, closed position wherein, when the spacer segments are extended, the sleeve is collapsed toward the main housing member to extend partially into the main housing member beyond the tube to properly position an aerosol medication container spray nozzle for medication dispensing therefrom.

In some preferred embodiments of the present invention spacer/holding chamber for pressurized metered dose inhaler, the sleeve has a shoulder that extends inwardly and the shoulder includes a container spray nozzle orifice.

In some preferred embodiments of the present invention spacer/holding chamber for pressurized metered dose inhaler, the tube has a one of a guide slot and a guide détente, and the sleeve has the other of a corresponding guide slot and a guide détente so as to limit the movement distance of the sleeve relative to the tube.

In some preferred embodiments of the present invention spacer/holding chamber for pressurized metered dose inhaler, the sleeve is tightly fitted into the tube so as to require pull and push force for reciprocal movement.

In some preferred embodiments of the present invention spacer/holding chamber for pressurized metered dose inhaler, the sleeve is freely fitted into the tube so as to utilize gravity for reciprocal movement.

In some preferred embodiments of the present invention spacer/holding chamber for pressurized metered dose inhaler, the spacer segments are interlocking collapsible, telescopic rings.

In some preferred embodiments of the present invention spacer/holding chamber for pressurized metered dose inhaler, the spacer segments are bellows segments.

In some preferred embodiments of the present invention spacer/holding chamber for pressurized metered dose inhaler, main housing member includes a one way valve that permits flow of medication out of the nozzle portion and prevents inward flow back into the main housing member.

In some preferred embodiments of the present invention spacer/holding chamber for pressurized metered dose inhaler, the sleeve includes the détente and the tube includes the guide slot.

In some preferred embodiments of the present invention spacer/holding chamber for pressurized metered dose inhaler, the nozzle portion includes a tethered cap connected thereto.

In other embodiments, the metered dosage inhaler device has a main housing member for receiving and dispensing inhalation medication, the main housing member being hollow, and having an aerosol medication container insertion end and having a nozzle end for spraying medication into a mouth of a user, wherein the nozzle end has a defined length and has an orifice with a defined cross-sectional area outlet surfaces, inner surfaces and a defined outer perimeter at its termination, and the improvement comprises: a spacer member fitted onto the nozzle and adapted to move outwardly and inwardly relatively to the nozzle, the spacer member being hollow and being located within the outer surfaces of the nozzle, the spacer member having a plurality of segments that, when fully collapsed; have a total length about equal to or less than the nozzle so as to preserve significant compactness; and, an aerosol medication container sleeve connected to and partially located inside the aerosol medication container tube, the sleeve being reciprocally slideable along the central axis and relative to the tube, the sleeve being adapted to receive and hold an aerosol medication container, the sleeve having a first, open position wherein the sleeve is extended away from the main housing member to create a maximum open internal volume for collapse of the spacer segments into the main housing, the sleeve having a second, closed position wherein, when the spacer segments are extended, the sleeve is collapsed toward the main housing member to extend partially into the main housing member beyond the tube to properly position an aerosol medication container spray nozzle for medication dispensing therefrom.

In some preferred embodiments of the present invention spacer/holding chamber for pressurized metered dose inhaler, the sleeve has a shoulder that extends inwardly and the shoulder includes a container spray nozzle orifice.

In some preferred embodiments of the present invention spacer/holding chamber for pressurized metered dose inhaler, the tube has a one of a guide slot and a guide détente, and the sleeve has the other of a corresponding guide slot and a guide détente so as to limit the movement distance of the sleeve relative to the tube.

In some preferred embodiments of the present invention spacer/holding chamber for pressurized metered dose inhaler, the sleeve is tightly fitted into the tube so as to require pull and push force for reciprocal movement.

In some preferred embodiments of the present invention spacer/holding chamber for pressurized metered dose inhaler, the sleeve is freely fitted into the tube so as to utilize gravity for reciprocal movement.

In some preferred embodiments of the present invention spacer/holding chamber for pressurized metered dose inhaler, the spacer segments are interlocking collapsible, telescopic rings.

In some preferred embodiments of the present invention spacer/holding chamber for pressurized metered dose inhaler, the spacer segments are bellows segments.

In some preferred embodiments of the present invention spacer/holding chamber for pressurized metered dose inhaler, main housing member includes a one way valve that permits flow of medication out of the nozzle portion and prevents inward flow back into the main housing member.

In some preferred embodiments of the present invention spacer/holding chamber for pressurized metered dose inhaler, the sleeve includes the détente and the tube includes the guide slot.

In some preferred embodiments of the present invention spacer/holding chamber for pressurized metered dose inhaler, the nozzle portion includes a tethered cap connected thereto.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings.

DETAILED DESCRIPTION OF THE EMBODIMENTS

Figure 1:
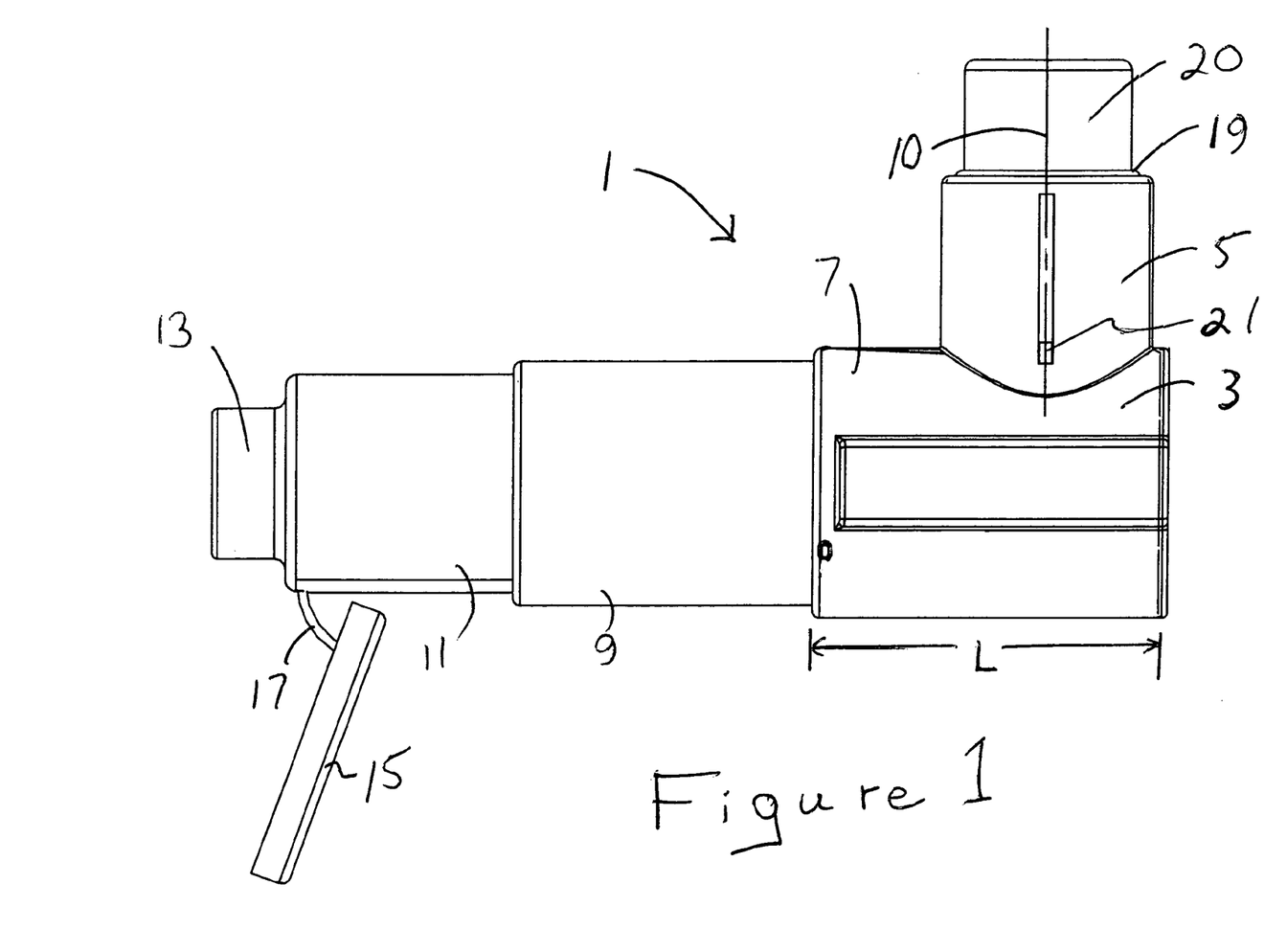
FIG. 1 is a side view of a preferred embodiment of a spacer/holding chamber for pressurized metered dose inhaler according to the present invention, shown in its open position for use.

FIG. 1 shows a side view of one preferred embodiment of a present invention spacer/holding chamber for pressurized metered dose inhaler 1. Spacer/holding chamber for pressurized metered dose inhaler 1 includes a main housing member 3 that is hollow and has an aerosol medication insertion tube 5 extending upwardly therefrom along central axis 10. Main housing member 3 has a nozzle segment 7 having a length L and an opening or orifice facing to the left into which telescopic spacer member segments 9 and 11 are slidably fitted. Mouthpiece 13 is at the outermost part of spacer member segment 11. Optional cap 15 with tether 17 is connected to spacer member segment 11 as shown. Optional cap 15 performs two functions—first, when the spacer member segments are collapsed (pushed in), cap 15 will seal mouthpiece 13 to protect it and keep it clean by snapping onto nozzle segment 7, and, second, it acts as a pull so that the spacer member segments may be extended without touching the mouthpiece.

Telescopically connected to nozzle segment 7 are the two spacer member segments 9 and 11. Although two segments are shown, three or more segments could be utilized without exceeding the scope of the present invention. Additionally, while mouthpiece 13 is a part of and integrally formed with segment 11, it could be a separate segment.

The side view shown in FIG. 1 of inhaler 1 is positioned in its open position ready for use. Thus, telescopic spacer member segments 9 and 11 are extended with cap is removed and mouth piece 13 available for insertion into a users mouth. Likewise, aerosol medication container 20 and aerosol medication sleeve 19 are down so that container 20 is ready to be pressed for medication release.

Figure 2:
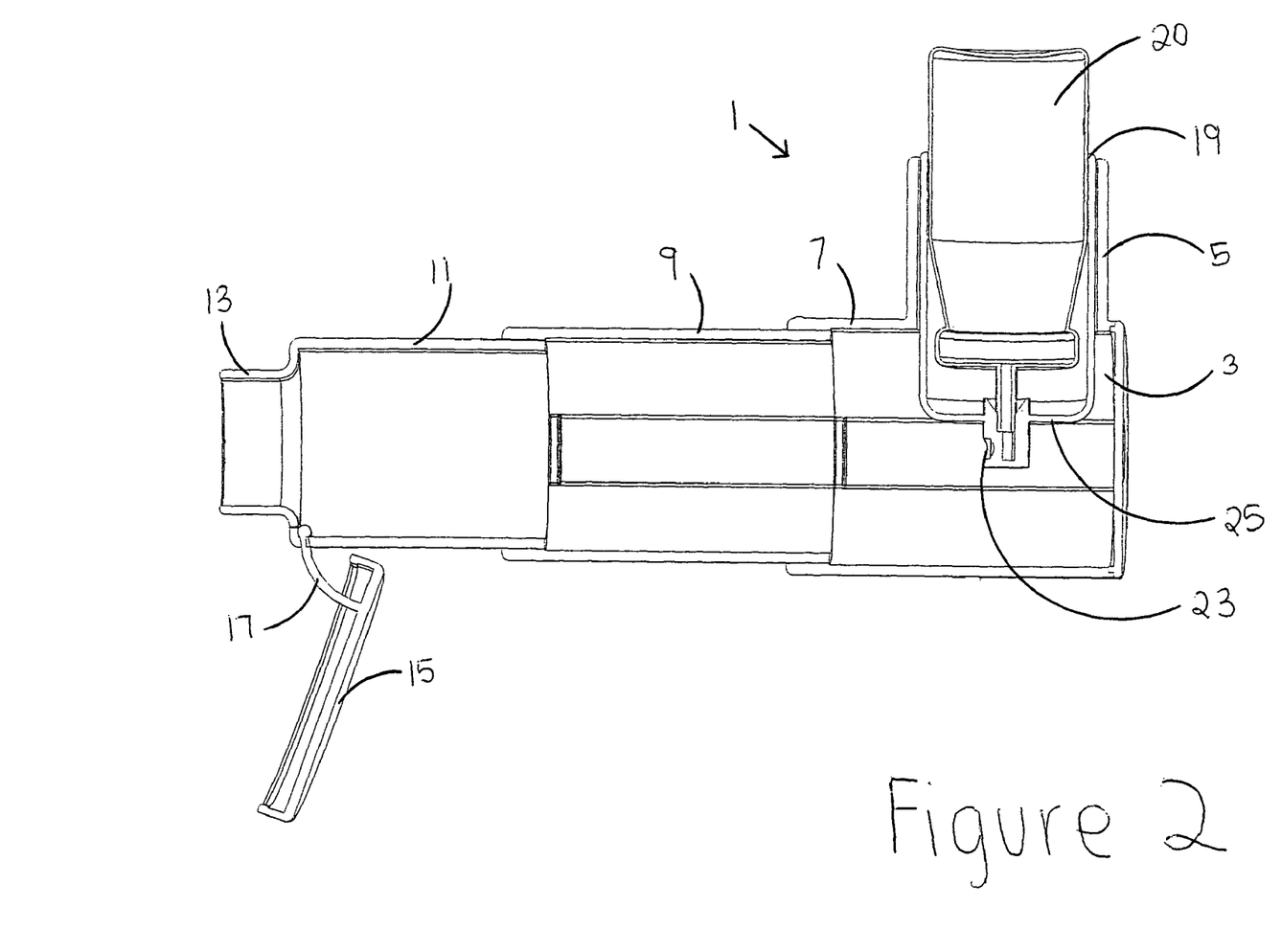
FIGS. 2 and 3 illustrate a cut side view and a front view of the present invention spacer/holding chamber for pressurized metered dose inhaler shown in FIG. 1.

Referring now to both FIGS. 1 and 2, sleeve 19 has a stop protrusion 21, a shoulder 25 and a container spray nozzle receiver with orifice 23. When a user inserts mouthpiece 13 into the mouth and presses on container 20, medication, is released via orifice 23 and the medication has sufficient volume within the extended segments to expand into a more effective body of air for inhalation of the user.

Figure 3:
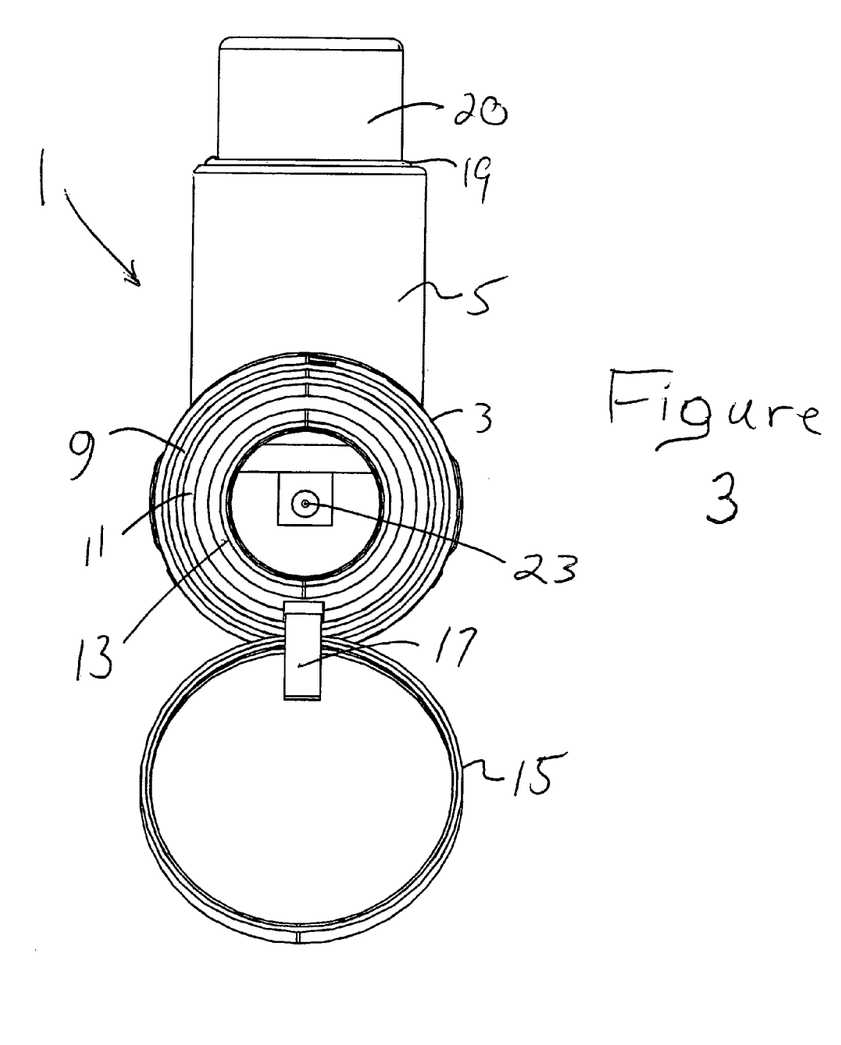

FIG. 3 shows a front view of inhaler 1 that is shown in FIGS. 1 and 2 and identical parts are identically numbered.

Figure 4:
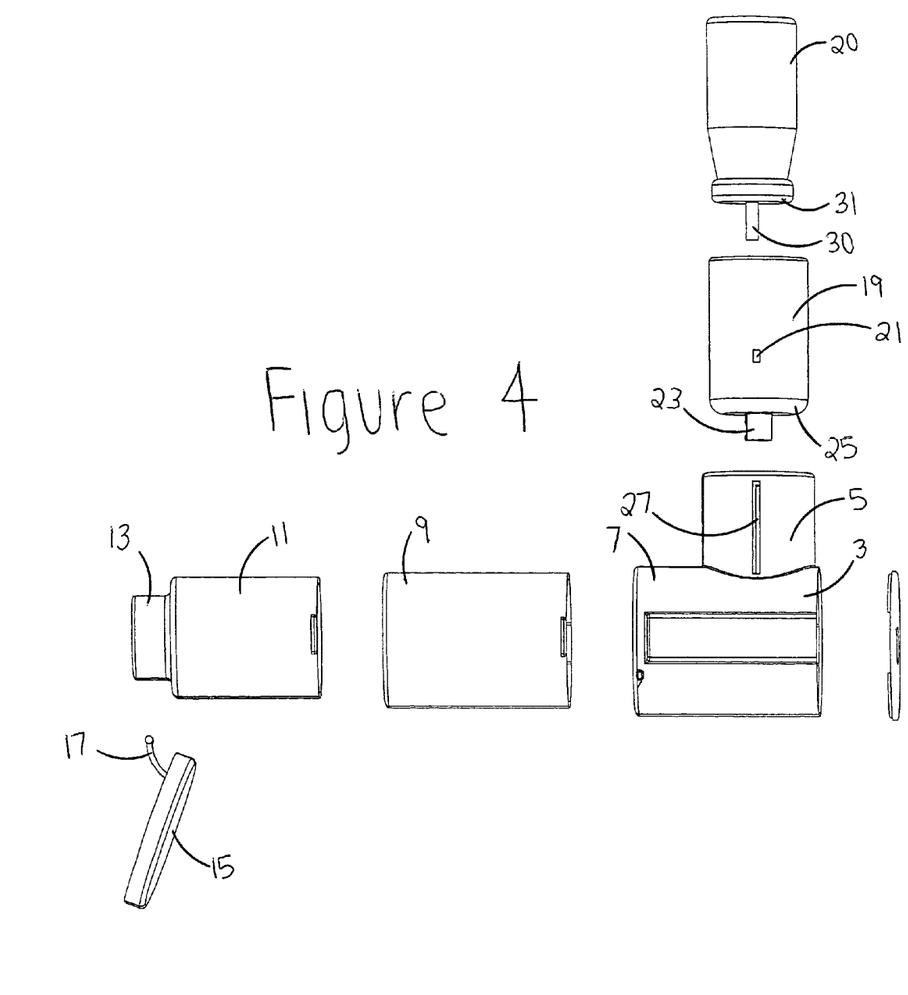
FIG. 4 shows an exploded side view of the present invention spacer/holding chamber for pressurized metered dose inhaler shown in FIG. 1.

FIG. 4 shows a side, exploded view of the present invention inhaler 1 shown in FIGS. 1 though 3 above. Identical parts are identically numbered. In this view, note that main housing member 3 has an open back end and a back end cover 29 that permanently fits onto main housing member 3 and may be permanently and sealably attached as by force fit, heat weld, ultrasonic weld or any other attachment means. Also, shown in this FIG. 4 is a protrusion 21 and a slide slot 27. This permits reciprocal movement of sleeve 19 within tube 5 along the length of slot 27 and prevents accidental removal of sleeve 19 from tube 5. Aerosol medication container 20 has a dispensing nozzle 30 and a top rim 31 that snuggly fits into sleeve 19. Likewise, nozzle 30 fits snuggly into its spray nozzle receiver with orifice 23, as shown in FIG. 2. When a user pulls on container 20 or pushes on container 20, sleeve 19 will move with it until the snug fit friction is overcome. Also, as shown in FIGS. 1, 2 and 3 sleeve 19 is in its down position for use. It may be pushed into this position or, alternatively, dropped into this position by gravity. By inverting or pulling up on sleeve 19, main housing member 3 is open for contraction of the nozzle segments 9 and 11. This is shown in FIGS. 5 and 6 below.

Figure 5:
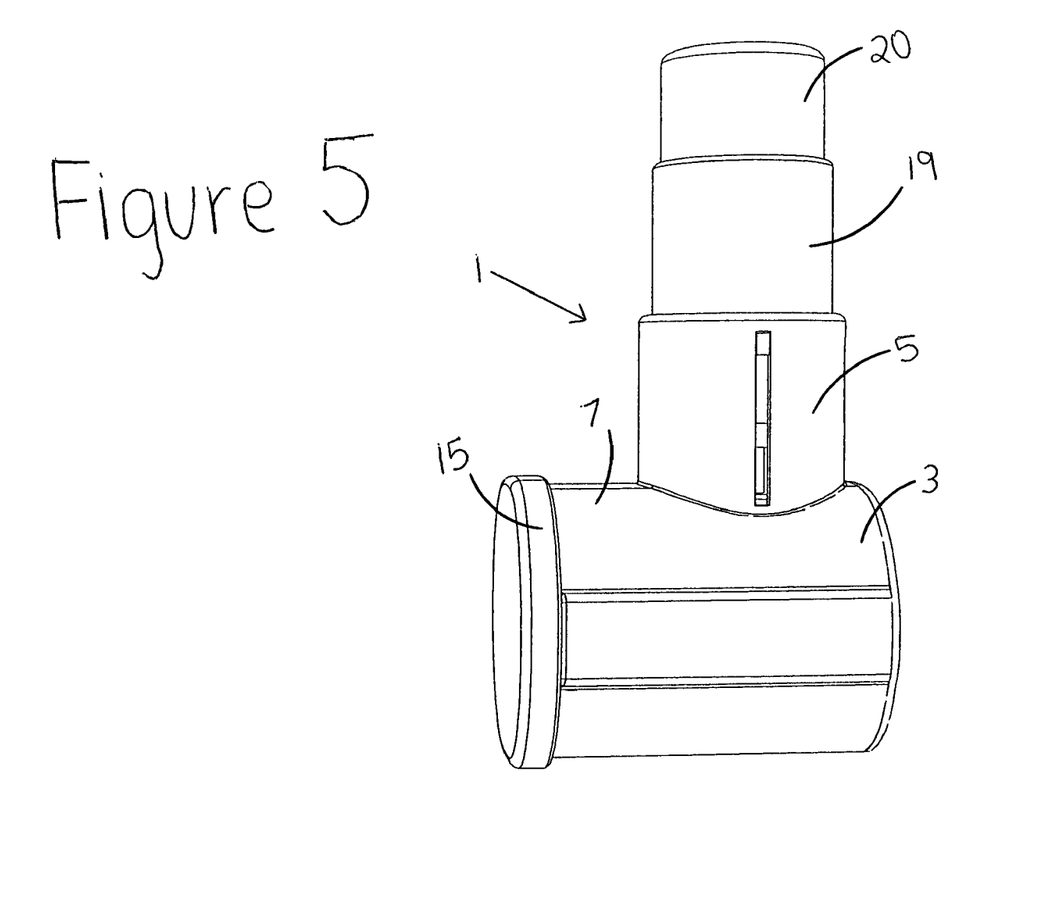
FIG. 5 shows a side view of the embodiment of the present invention spacer/holding chamber for pressurized metered dose inhaler shown in FIG. 1, but in its closed position.
Figure 6:
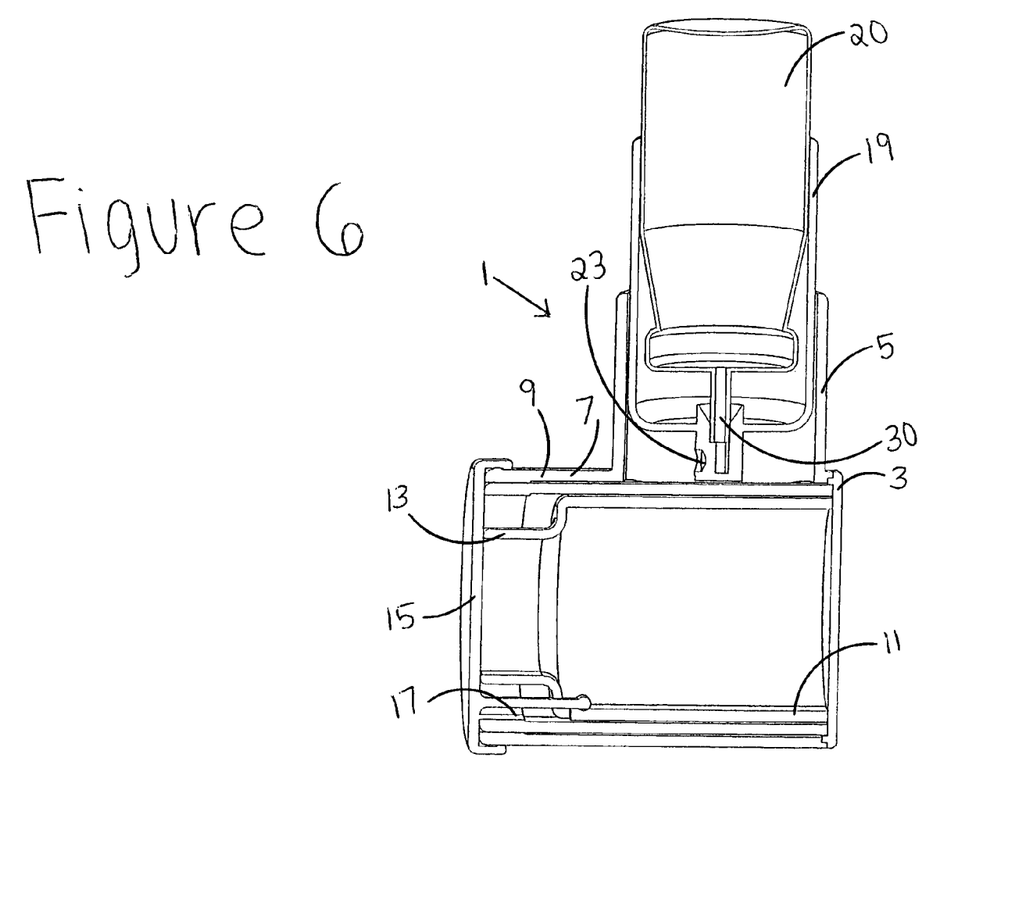
FIG. 6 shows a side cut view of the present invention spacer/holding chamber for pressurized metered dose inhaler shown in FIG. 5.

FIGS. 5 and 6 show a side view and a cut side view, respectively, of inhaler 1 shown and described above. However, in these Figures, sleeve 19 is in its up position and nozzle segments 9 and 11 have been pushed all the way into main housing member 3 and cap 15 has been attached thereto to protect mouthpiece 13, to prevent accidental extension of the nozzle segments and to present an extremely compact device for pocket, pocketbook or other storage. Thus, it is an object of the present invention to substantially eliminate, and in preferred embodiments, completely eliminate any added length resulting from a spacer, and this object is achieved as described above.

Obviously, numerous modifications and variations of the present invention are possible in light of the above teachings. For example, the segments used in the spacers need not be circular and in some cases it is desirable that they be non-circular. As another example, the present invention devices may include a separator disc with a one way valve that permits flow from but not back into the main housing.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

What is claimed is:

1. In a pressurized metered dosage inhaler device having a main housing member for receiving and dispensing inhalation medication, said main housing member being hollow, and having an aerosol medication container insertion tube and a central axis of direction of insertion of an aerosol medication container, and having a nozzle portion for spraying medication into a mouth of a user, said nozzle portion extending away from said central axis, wherein said nozzle portion includes a nozzle segment that is exterior from said main housing member and has a defined length L, and has an orifice with a defined cross-sectional area outer surfaces, inner surfaces, the improvement which comprises:

(a) a spacer member, said spacer member being fitted onto said nozzle segment and adapted to move outwardly and inwardly relatively to said nozzle segment, said spacer member being hollow and being located about said outer surfaces of said nozzle segment, said spacer member including a plurality of moveable segments, each of said moveable segments being interconnected with one another, said spacer member having an open extended position with said moveable segments being extended relative to one another to create an elongated spacer member, wherein an outermost extended segment is a mouthpiece segment, and said spacer member having a closed position wherein all of said moveable segments are collapsed relative to one another such that all moveable segments are located about said nozzle, so as to have a total length equal to or less than exterior nozzle segment length L so as to eliminate protrusion beyond said nozzle segment, and so as to preserve significant compactness when said spacer member is moved inwardly relative to said nozzle; and, (b) an aerosol medication container sleeve connected to and partially located inside said aerosol medication container tube, said sleeve being reciprocally slideable along said central axis and relative to said tube, said sleeve being adapted to receive and hold an aerosol medication container, said sleeve having a first, open position wherein said sleeve is extended away from said main housing member to create a maximum open internal volume for collapse of said spacer segments into said main housing, said sleeve having a second, closed position wherein, when said spacer segments are extended, said sleeve is collapsed toward said main housing member to extend partially into said main housing member beyond said tube to properly position an aerosol medication container spray nozzle for medication dispensing therefrom.

2. The device of claim 1 wherein said sleeve has a shoulder that extends inwardly and said shoulder includes a container spray nozzle orifice.

3. The device of claim 1 wherein said tube has a one of a guide slot and a guide détente, and said sleeve has the other of a corresponding guide slot and a guide détente so as to limit the movement distance of said sleeve relative to said tube.

4. The device of claim 1 wherein said sleeve is tightly fitted into said tube so as to require pull and push force for reciprocal movement.

5. The device of claim 1 wherein said sleeve is freely fitted into said tube so as to utilize gravity for reciprocal movement.

6. The device of claim 1 wherein said spacer segments are interlocking collapsible, telescopic rings.

7. The device of claim 1 wherein said spacer segments are bellows segments.

8. The device of claim 1 wherein main housing member includes a one way valve that permits flow of medication out of said nozzle portion and prevents inward flow back into said main housing member.

9. The device of claim 1 wherein said sleeve includes said détente and said tube includes said guide slot.

10. The device of claim 1 wherein said nozzle portion includes a tethered cap connected thereto.

11. In a metered dosage inhaler device having a main housing member for receiving and dispensing inhalation medication, said main housing member being hollow, and having an aerosol medication container insertion end and having a nozzle end for spraying medication into a mouth of a user, wherein said nozzle end has a defined length and has an orifice with a defined cross-sectional area outlet surfaces, inner surfaces and a defined outer perimeter at its termination, the improvement which comprises:
   (a) a spacer member fitted onto said nozzle and adapted to move outwardly and inwardly relatively to said nozzle, said spacer member being hollow and being located within said outer surfaces of said nozzle, said spacer member having a plurality of segments that, when fully collapsed, have a total length about equal to or less than said nozzle so as to preserve significant compactness; and,
   (b) an aerosol medication container sleeve connected to and partially located inside said aerosol medication container tube, said sleeve being reciprocally slideable along said central axis and relative to said tube, said sleeve being adapted to receive and hold an aerosol medication container, said sleeve having a first, open position wherein said sleeve is extended away from said main housing member to create a maximum open internal volume for collapse of said spacer segments into said main housing, said sleeve having a second, closed position wherein, when said spacer segments are extended, said sleeve is collapsed toward said main housing member to extend partially into said main housing member beyond said tube to properly position an aerosol medication container spray nozzle for medication dispensing therefrom.

12. The device of claim 11 wherein said sleeve has a shoulder that extends inwardly and said shoulder includes a container spray nozzle orifice.

13. The device of claim 11 wherein said tube has a one of a guide slot and a guide détente, and said sleeve has the other of a corresponding guide slot and a guide détente so as to limit the movement distance of said sleeve relative to said tube.

14. The device of claim 11 wherein said sleeve is tightly fitted into said tube so as to require pull and push force for reciprocal movement.

15. The device of claim 11 wherein said sleeve is freely fitted into said tube so as to utilize gravity for reciprocal movement.

16. The device of claim 11 wherein said spacer segments are interlocking collapsible, telescopic rings.

17. The device of claim 11 wherein said spacer segments are bellows segments.

18. The device of claim 11 wherein main housing member includes a one way valve that permits flow of medication out of said nozzle portion and prevents inward flow back into said main housing member.

19. The device of claim 11 wherein said sleeve includes said détente and said tube includes said guide slot.

20. The device of claim 11 wherein said nozzle portion includes a tethered cap connected thereto.

* * * * *